United States Patent
Latterell

(10) Patent No.: US 8,636,687 B1
(45) Date of Patent: Jan. 28, 2014

(54) TISSUE SEALING METHOD

(75) Inventor: Scott T. Latterell, Hermosa Beach, CA (US)

(73) Assignee: Spinnaker Medical LLC, Hermosa Beach, CA (US)

( * ) Notice: Subject to any disclaimer, the term of this patent is extended or adjusted under 35 U.S.C. 154(b) by 705 days.

(21) Appl. No.: 12/398,300

(22) Filed: Mar. 5, 2009

Related U.S. Application Data

(60) Provisional application No. 61/068,246, filed on Mar. 6, 2008.

(51) Int. Cl.
*A61B 18/18* (2006.01)
*A61B 18/04* (2006.01)

(52) U.S. Cl.
USPC .................. 604/41; 604/51; 604/32; 604/34; 604/40; 604/49

(58) Field of Classification Search
USPC .......................... 606/1, 32, 41, 49, 50–52, 40
See application file for complete search history.

(56) References Cited

U.S. PATENT DOCUMENTS

| | | | | |
|---|---|---|---|---|
| 5,674,220 A * | 10/1997 | Fox et al. | | 606/51 |
| 6,113,598 A * | 9/2000 | Baker | | 606/51 |
| 6,514,252 B2 * | 2/2003 | Nezhat et al. | | 606/48 |
| 7,160,298 B2 | 1/2007 | Lawes et al. | | |
| 2005/0021025 A1 * | 1/2005 | Buysse et al. | | 606/51 |
| 2006/0217697 A1 * | 9/2006 | Lau et al. | | 606/29 |
| 2011/0087209 A1 * | 4/2011 | Boudreaux et al. | | 606/29 |

* cited by examiner

*Primary Examiner* — Emily Schmidt
*Assistant Examiner* — Bradley G Thomas, Jr.
(74) *Attorney, Agent, or Firm* — Pauly, Devries, Smith & Deffner, L.L.C.

(57) ABSTRACT

An improved method and equipment for tissue/vessel sealing is disclosed for the sealing, coagulation and transection of tissue during surgical procedures. The improvement is accomplished through better management of heat and moisture present during tissue treatment by having tissue grasping surfaces comprised of an outer non-conducting region and an inner conductive region, and including channels in the jaw assembly to direct steam and moisture away from surrounding tissue. The outer region follows the perimeter each jaw, isolating the treatment zone and preventing steam and excess heat from leaving the tissue treatment zone, reducing thermal margins and unintended patient burns. The outer region also prevents surrounding moisture from affecting the treatment zone and allowing more consistent results.

17 Claims, 4 Drawing Sheets

TISSUE SEALING METHOD

RELATED CASES

This application claims priority to U.S. Provisional Application Ser. No. 61/068,246, filed Mar. 6, 2008, the content of which is herein incorporated by reference in its entirety.

FIELD OF THE INVENTION

The present invention is in the technical field of electrosurgical medical devices. More particularly, the present invention relates to devices used for the coagulation and sealing of vessels and tissue utilizing radio-frequency (RF) energy during open or laparoscopic surgical procedures.

BACKGROUND OF THE INVENTION

Devices used for the coagulation and sealing of vessels often utilizes heat generated by bipolar RF energy combined with clamping pressure to electrosurgically seal blood vessels and tissue as required during both open and laparoscopic surgical procedures. This process has become well accepted and replaces the use of sutures, clips and staples in many instances, reducing procedure time and cost.

However, consistent performance is a common issue with these types of devices, resulting in failed seals, blood loss and safety concerns. In addition, many instances of excessive energy delivery at the seal site results in over desiccated, charred tissue, sticking and unintended thermal damage to surrounding tissue structures. A major cause of unintended tissue damage is the generation of boiling fluid and steam during the sealing process. This hot vapor and fluid is released under pressure along the outer periphery of the jaws and can damage tissue more than 10 mm away from the target site. Because of this, improvements in reliability, performance and safety are very desirable to the surgeon.

BRIEF SUMMARY OF THE INVENTION

The present invention relates to improved RF tissue coagulation and sealing by having better control of the target tissue area. This is accomplished by incorporating seal features outside of the clamp region to prevent heat, in the form of steam or hot fluid, from escaping outside of the clamped region and directing it back through the jaws of the device, into the treatment area instead of away from the site. Heat that was previously wasted or caused undesired damage by escaping is more efficiently used in the target region.

Because the heating of tissue and the generation of steam results in a large pressure increase at the target site, one or more inner channels can be located within the jaw assembly to provide pressure relief and direct exhaust out the back of the jaws and away from nearby tissue. The results of utilizing this wet heat are faster, more consistent results, reduced char and sticking, and better precision. Also, by channeling steam and the resulting excess heat away from the site and through the instrument, inadvertent burns to the patient and physician will be reduced.

Additionally, the disclosed invention prevents excess moisture outside of the target area to adversely effect energy delivery, a common problem of current sealing systems. During laparoscopic procedures visibility can be improved by the reduction of mist and particles in the operative cavity as well as a reduction in camera lens fogging. Further, exhaust can be filtered, reducing concerns over surgical plume. The disclosed invention also allows for the temperature monitoring of exhaust to aid in the control of energy delivery from the RF generator.

DETAILED DESCRIPTION OF THE INVENTION

Figure 1:
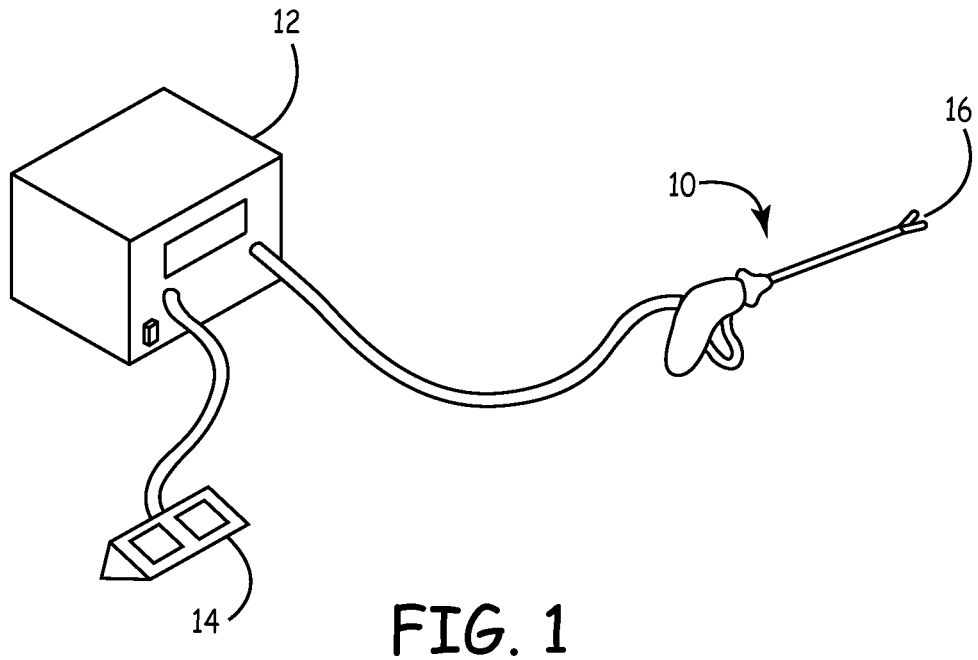
FIG. 1 illustrates an existing electrosurgical vessel sealing system.
Figure 2:
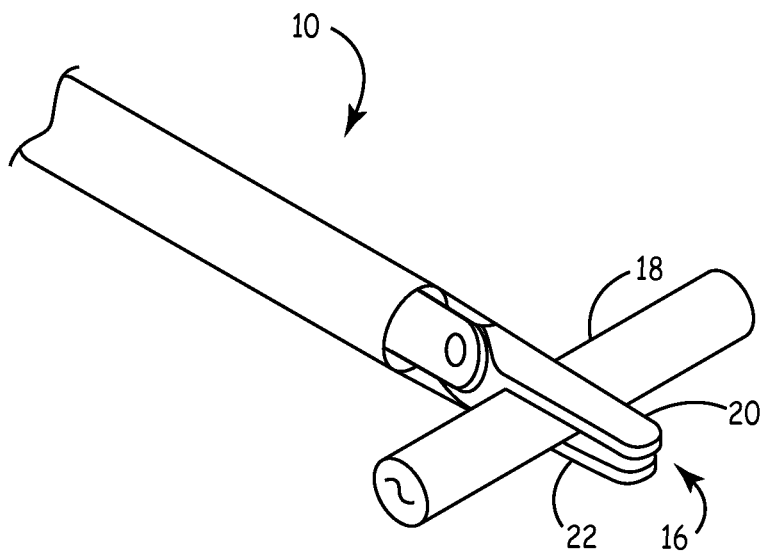
FIG. 2 illustrates an existing electrosurgical vessel sealing device.

Referring now to the invention in more detail, in FIG. 1 there is shown a typical vessel sealing system with a device 10 connected to an electro-surgical generator 12 with energy being delivered to target tissue through the device's distal tip 16 by activating a footswitch 14. FIG. 2 illustrates further detail of a current sealing device 10 with a vessel 18 clamped between jaws 20 and 22 located at the distal tip 16 delivering the need pressure for sealing.

Figure 3:
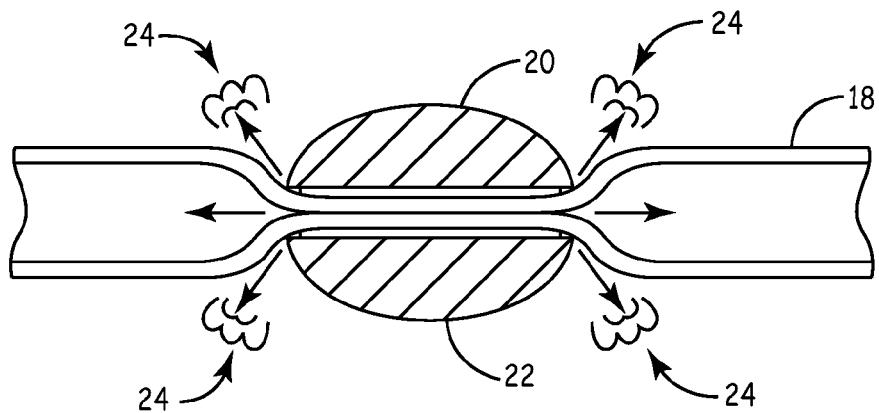
FIG. 3 illustrates a cross-sectional view of vessel sealing action of an existing device.

Referring now to more detail of current sealing devices, in FIG. 3 there is shown a cross-section of a vessel 18 grasped between jaws 20 and 22 with sufficient clamp force.

To seal the vessel 18 RF energy is delivered between jaws 20 and 22 and through the tissue clamped between them. The flow of energy heats moisture in the tissue to the boiling point and it is through this heat and pressure that the vessel is permanently sealed. However, a large amount of heat escapes the seal zone along the outside jaw-tissue interface in the form of steam 24 and boiling fluid. This escaping heat can injure tissue over 10 mm away from the jaws and as moisture is driven out of the seal zone, over desiccation and sticking occur.

Figure 4:
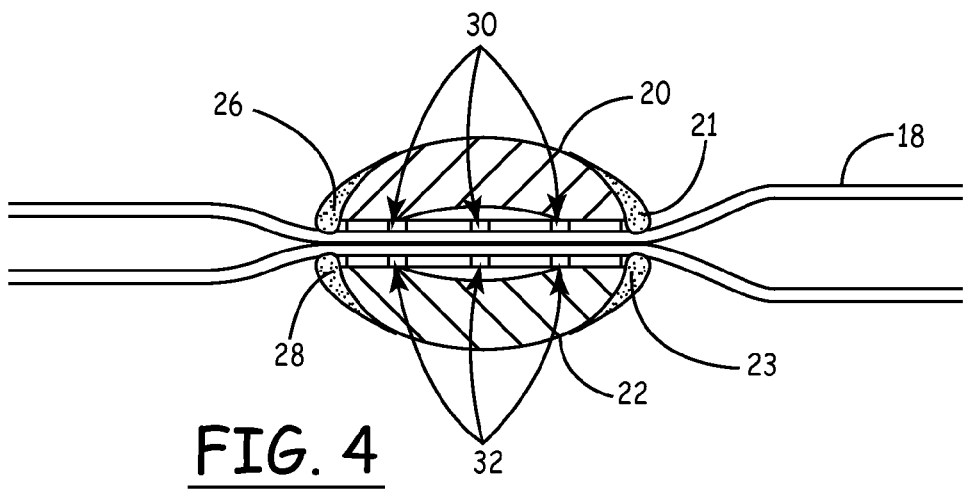
FIG. 4 illustrates a cross-sectional view of the present invention.

Referring now to the invention, shown in FIG. 4 are opposing jaws 20 and 22 clamping a vessel 18. Located along the entire outer perimeter of each jaw 20 and 22 are apposing elastomeric compression/seal regions 26 and 28. These non-heating sealing features extend beyond the seal surfaces 21 and 23 of the jaws 20 and 22, coming into first contact with tissue 18 and compressing on the tissue just outside of the sealing zone, creating a barrier to escaping heat/steam. Channels 30 and 32 located on each jaw 20 and 22 direct steam pressures back through the seal zone and out the back of the jaw and away from adjacent structures. By blocking its escape, heat is retained within the sealing zone longer, providing more consistent seals faster, and with less energy.

In addition, the outer barriers 26 and 28 retain moisture in the tissue seal zone, preventing over desiccation and sticking of tissue 18 to the jaws 20 and 22. Blocking of escaping heat also prevents damage to tissue outside the seal zone, allowing the physician to operate in closer proximity to critical tissue structures. Additionally, it is understood that the seal regions of the jaws may be in the form of a conductive material mounted to the jaw or the jaws themselves may form this conductive surface. It is also understood that exhaust may be directed out the top outer surface of the jaws rather than the back, but this is not preferred.

The above described sealing features have the additional benefit of keeping excess moisture in the form of blood and/or irrigation fluid from interfering with delivery of the energy needed to properly seal tissue. Excess fluid can steal a tremendous amount of the RF energy being delivered, greatly increasing time to complete the seal. In addition many RF electro-surgical systems that utilize impedance (resistance) sensing features to control energy delivery and even indicate successful completion of tissue sealing. Excess fluid hampers such systems and can even give false indication of a good seal, resulting potential bloodloss.

Figure 5:
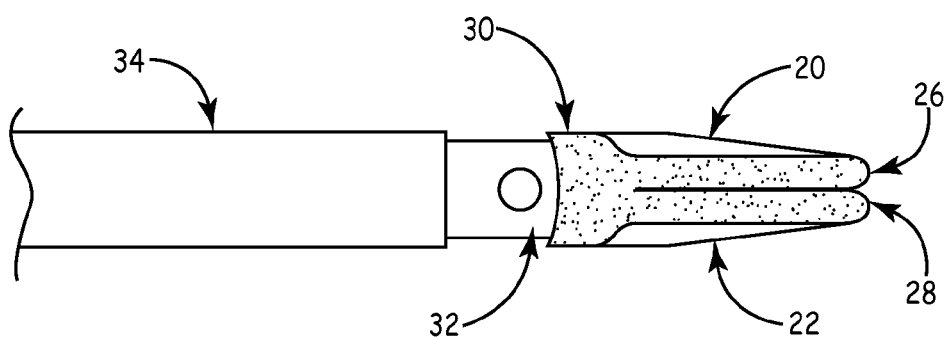
FIG. 5 illustrates a side view of current invention

Referring to more detail of the invention, FIG. 5 shows a side view of the jaws 20 and 22 with mechanical sealing features 26 and 28 extending towards the back of the jaws and connecting to form a hinge 30 in the jaw pivot region 32 behind the sealing surfaces of the jaws. Additionally, but not shown, elastomeric material behind seal zone 30 can be extended back over the device shaft 34 to direct exhaust further from site.

Figure 6:
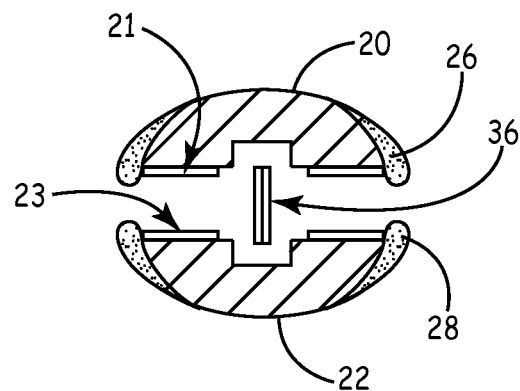
FIG. 6 illustrates a self-tensioning version of the current invention incorporated into a sealing, cutting device in an open-jaw position.
Figure 7:
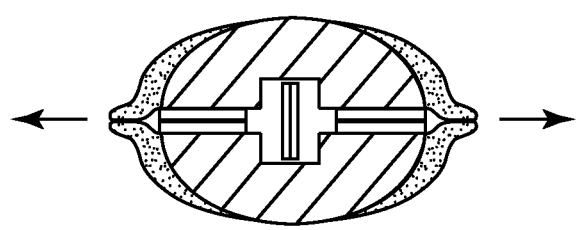
FIG. 7 illustrates a self-tensioning version of the current invention incorporated into a sealing, cutting device with the jaws closed.

Referring now to FIG. 6, the invention is incorporated into a known sealing device with a blade 36 to mechanically cut sealed tissue. In this configuration, in addition to extending beyond the seal surfaces 21 and 23, the elastomeric seal features 26 and 28 are shaped to provide tension to the tissue for aiding in transection when the jaws are closed as shown in FIG. 7. It is understood that cutting can be accomplished electro-surgically as well. It can also be seen from FIG. 6 and FIG. 7. that having the sealing features 26 and 28 extend to a height beyond the seal surfaces 21 and 23 will aid tissue release upon opening of the jaws.

Figure 8:
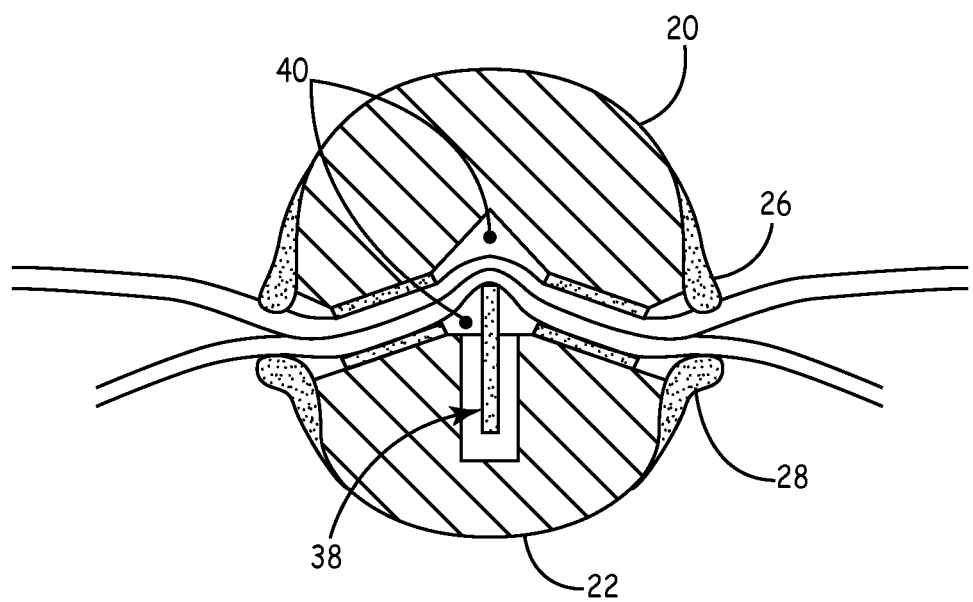
FIG. 8 illustrates a version of the current invention with electro-surgical transection, including a moisture retention feature located in the transection region

Referring now to FIG. 8, the invention is incorporated into a sealing device with a separate electrode 38 to electro-surgically cut sealed tissue. Also incorporated into the configuration is a moisture retaining feature 40, which may or may not be a pressure directing channel, located where electro-surgical transection is to take place. By retaining moisture in this region it is much easier and faster to transect tissue electro-surgically, and at lower energy levels.

The advantages of the present invention include in certain embodiments, without limitation, a reduction in the thermal margin and unintended tissue damage created by existing modalities when coagulating or sealing tissue. The management of heat and moisture also improves seal consistency while reducing energy requirements, reduces sticking and charring of tissue, and improves the surgical field of vision. Furthermore, when used with devices incorporating tissue cutting, the invention will aid in the transection/cutting of tissue by providing tension to the target tissue.

It is well within the skill of a person in the technical field, upon becoming conversant with, or otherwise having knowledge of, the present invention, to select suitable combinations of jaw and electrode components, elastomer configurations, and the like, in view of the type of tissue treatment device being designed and/or constructed.

The above described embodiments are exemplitive, and the terminology is employed for illustration purposes and not limitation purposes. The present invention is not limited to the combinations and sub-combinations illustrated herein.

I claim:

1. An electrosurgical instrument for treatment of tissue with distal end effectors comprising:

i. a jaw assembly of paired first and second opposing jaw members moveable between an open and closed position for grasping and delivering energy to target tissue, the jaw assembly having a distal end forming a tip of the jaw assembly and a proximal end opposite the distal end;
  ii. at least one jaw member having an inner area of its grasping surface that is conductive for the sealing of tissue;
  iii. at least one jaw member containing an outer region on the entire perimeter of the jaw's grasping surface that is non-conductive, and the outer region configured to apply a sealing force around the perimeter of the jaw, the sealing force sufficient to prevent the substantial escape of steam from the tissue treatment site during application of electrical energy, and
  iv. said jaw assembly containing at least one channel in the jaw assembly configured to provide pressure relief by directing generated heat and moisture back within the jaw assembly toward the proximate end of the jaw assembly.

2. The jaw assembly of claim 1 where the pressure directing feature comprises at least one channel in at least one of jaw.

3. The jaw assembly 2, wherein the pressure directing feature is located at the interface of the conductive and non-conductive portions of the grasping surface of at least one jaw, following the perimeter shape of the jaw.

4. The jaw assembly 2, wherein the pressure directing feature is located in the conductive grasping region of at least one jaw.

5. The jaw assembly 2, wherein the pressure directing feature comprises a pattern in the form of channels or openings traveling from the non-conducting grasping surface of the jaws inward, through the conductive portion of the jaws.

6. The jaw assembly of claim 1 configured so that excess heat and pressure are directed to exhaust out the back region of the jaw assembly.

7. The jaw assembly of claim 1 configured so that excess heat and pressure are directed to exhaust through the shaft or body of the instrument.

8. The jaw assembly of claim 1 configured so that excess heat and pressure are directed to exhaust out the outer middle surface of at least one jaw.

9. The jaw assembly of claim 1 where the outer, non-conductive grasping surface is configured to come into tissue contact prior to the inner, conductive region of the grasping surface and provide sufficient pressure to prevent steam and other hot moisture from escaping the outer perimeter of jaws.

10. The jaw assembly of claim 1 where the outer, non-conductive grasping surface is configured to come into tissue contact at the same time as the inner, conductive region of the grasping surface and provide sufficient pressure to prevent steam and other hot moisture from escaping the outer perimeter of jaws.

11. The jaw assembly of claim 1 where the outer, non-conductive grasping surface is configured to come into tissue contact after the inner, conductive region of the grasping surface and provide sufficient pressure to prevent steam and other hot moisture from escaping the outer perimeter of jaws.

12. The jaw assembly of claim 1 where the outer, non-conductive region of the grasping surface is configured to provide an inside to out tensioning of tissue being grasped.

13. The jaw assembly of claim 1 where the outer, non-conductive region of the grasping surface is moveable in relation to the inner, conductive region.

14. The jaw assembly of claim 1 where the outer, non-conductive region of the grasping surface is in the form of an elastomeric material.

15. The jaw assembly of claim 1 where the outer, non-conductive region of the grasping surface provides a physical and electrical barrier to conductive fluids outside of the tissue grasp region.

16. The jaw assembly of claim 1 where the outer, non-conductive regions of the grasping surfaces contain surface features to aid in tissue retraction.

17. The jaw assembly of claim 1 where the outer, non-conductive region of the grasping surface is configured to aid in the release of treated tissue.

\* \* \* \* \*